United States Patent
Saing

(10) Patent No.: US 10,251,745 B2
(45) Date of Patent: *Apr. 9, 2019

(54) CONNECTOR FOR ATTACHING TISSUE TO BONE

(71) Applicant: ALBERT EINSTEIN HEALTHCARE NETWORK, Philadelphia, PA (US)

(72) Inventor: Minn Saing, Pompano Beach, FL (US)

(73) Assignee: ALBERT EINSTEIN HEALTHCARE NETWORK, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/901,425

(22) Filed: Feb. 21, 2018

(65) Prior Publication Data

US 2018/0177585 A1 Jun. 28, 2018

Related U.S. Application Data

(63) Continuation of application No. 15/245,873, filed on Aug. 24, 2016, now Pat. No. 9,931,196.

(Continued)

(51) Int. Cl.
*A61F 2/08* (2006.01)

(52) U.S. Cl.
CPC ..... *A61F 2/0811* (2013.01); *A61F 2002/0835* (2013.01); *A61F 2002/0858* (2013.01); *A61F 2002/0882* (2013.01)

(58) Field of Classification Search
CPC .. A61F 2/08; A61F 2/0811; A61F 2002/0835; A61F 2002/0858; A61F 2002/0882
See application file for complete search history.

(56) References Cited

U.S. PATENT DOCUMENTS

| | | |
|---|---|---|
| 3,176,316 A | 4/1965 | Bodell |
| 3,693,617 A | 9/1972 | Trott |

(Continued)

OTHER PUBLICATIONS

M. Collette, X. Cassard, The Tape Locking Screw technique (TLS): A new ACL reconstruction method using a short hamstring graft, Orthopaedics & Traumatology: Surgery & Research (2011) 97, 555-559.

(Continued)

*Primary Examiner* — Alvin Stewart
(74) *Attorney, Agent, or Firm* — Donald R. Piper, Jr.; Dann, Dorfman, Herrell & Skillman, P.C.

(57) ABSTRACT

A connector for attaching a connective tissue to bone includes a sling for supporting and holding the connective tissue. A trap generally cooperates with the sling. The trap includes an anchor end and a sling end and a generally tubular section configured to decrease in diameter upon application of a longitudinal tensile force. The trap is dimensioned to fit within a tunnel through bone so that the connective tissue emerges from one end of the tunnel and so that an interference screw can be inserted into the tubular section at the anchor end of the trap at the other end of the tunnel whereby a pulling force exerted on the sling causes the generally tubular section of the trap to constrict more tightly about the interference screw to prevent slippage and to deter withdrawal of the trap from the tunnel.

11 Claims, 3 Drawing Sheets

Related U.S. Application Data

(60) Provisional application No. 62/210,043, filed on Aug. 26, 2015.

(56) References Cited

U.S. PATENT DOCUMENTS

| | | |
|---|---|---|
| 3,797,047 A | 3/1974 | Pillet |
| 3,872,861 A | 3/1975 | Tamny |
| 3,883,102 A | 5/1975 | Trigg |
| 4,149,277 A | 4/1979 | Bokros |
| 4,255,820 A | 3/1981 | Rothermel |
| 4,321,854 A | 3/1982 | Foote |
| 4,604,821 A | 8/1986 | Moser |
| 4,640,179 A | 2/1987 | Cameron |
| 4,668,233 A | 5/1987 | Seedhom |
| 4,790,850 A | 12/1988 | Dunn |
| 4,917,699 A | 4/1990 | Chervitz |
| 4,917,700 A | 4/1990 | Aikins |
| 4,966,167 A | 10/1990 | Jacobs |
| 5,171,274 A | 12/1992 | Fluckiger |
| 5,358,498 A | 10/1994 | Shave |
| 5,456,721 A | 10/1995 | Legrand |
| 5,549,676 A | 8/1996 | Johnson |
| 5,984,926 A | 11/1999 | Jones |
| 6,099,530 A | 8/2000 | Simonian |
| 6,143,029 A | 11/2000 | Rippstein |
| 6,190,411 B1 | 2/2001 | Lo |
| 6,203,572 B1 | 3/2001 | Johnson et al. |
| 6,602,290 B2 | 8/2003 | Esnouf |
| 6,746,483 B1 | 6/2004 | Bojarski |
| 7,279,008 B2 | 10/2007 | Brown |
| 7,407,512 B2 | 8/2008 | Bojarski |
| 7,494,506 B2 | 2/2009 | Brulez |
| 8,088,130 B2 | 1/2012 | Kaiser |
| 8,333,803 B2 | 12/2012 | Park |
| 8,460,350 B2 | 6/2013 | Albertorio |
| 8,945,218 B2 | 2/2015 | Laurencin |
| 9,011,533 B2 | 4/2015 | Gadikota |
| 9,204,959 B2 | 12/2015 | Perriello |
| 9,247,936 B2 | 2/2016 | Sengun |
| 9,414,833 B2 | 8/2016 | Stone |
| 9,681,940 B2 | 6/2017 | Stone |
| 9,757,119 B2 | 9/2017 | Norton |
| 9,770,323 B2 | 9/2017 | Gadikota |
| 9,801,708 B2 | 10/2017 | Denham |
| 9,833,230 B2 | 12/2017 | Stone |
| 9,931,196 B2 * | 4/2018 | Saing .................. A61F 2/0811 |
| 2002/0055749 A1 | 5/2002 | Esnouf |
| 2004/0267362 A1 | 12/2004 | Hwang |
| 2007/0162121 A1 | 7/2007 | Tarrant |
| 2009/0240104 A1 | 9/2009 | Ogdahl |
| 2010/0292792 A1 | 11/2010 | Stone |
| 2011/0184227 A1 | 7/2011 | Altman |
| 2011/0288566 A1 | 11/2011 | Kubiak |
| 2012/0041496 A1 | 2/2012 | Walker |
| 2012/0109299 A1 | 5/2012 | Li |
| 2012/0150297 A1 | 6/2012 | Denham |
| 2012/0203253 A1 | 8/2012 | Kubiak |
| 2013/0013065 A1 | 1/2013 | Bills |
| 2013/0090731 A1 | 4/2013 | Walker |
| 2013/0345810 A1 | 12/2013 | Jaeger |
| 2014/0081320 A1 | 3/2014 | Sengun |
| 2014/0081325 A1 | 3/2014 | Sengun |
| 2014/0114412 A1 | 4/2014 | Landry |
| 2014/0121700 A1 | 5/2014 | Dreyfuss et al. |
| 2014/0257349 A1 | 9/2014 | Sudekum |
| 2014/0277121 A1 | 9/2014 | Pilgeram et al. |
| 2014/0296979 A1 | 10/2014 | Delfosse |
| 2015/0196384 A1 | 7/2015 | Niu et al. |
| 2016/0120639 A1 | 5/2016 | Murray |
| 2016/0193033 A1 | 7/2016 | Murray |
| 2016/0296105 A1 | 10/2016 | Ramsey |
| 2016/0324389 A1 | 11/2016 | Mangano |
| 2016/0332481 A1 | 11/2016 | Spanjers |
| 2016/0367391 A1 | 12/2016 | Paulos |
| 2017/0056158 A1 | 3/2017 | Saing |
| 2017/0165077 A1 | 6/2017 | McDonnell |
| 2017/0224326 A1 | 8/2017 | Burkhart |

OTHER PUBLICATIONS

International Search Report and Written Opinion of the International Searching Authority for PCT/US2016/048365 dated Oct. 28, 2016, 14 Pages.

* cited by examiner

CONNECTOR FOR ATTACHING TISSUE TO BONE

CROSS-REFERENCE TO RELATED APPLICATIONS

This application is a continuation of U.S. patent application Ser. No. 15/245,873 filed Aug. 24, 2016, which claims priority of U.S. Provisional Application No. 62/210,043 filed Aug. 26, 2015, the entire disclosure of which is incorporated by reference herein.

FIELD OF THE INVENTION

The present invention relates generally to a method and device for attaching tissue to bone and, more specifically, to a method and device for attaching connective tissue to bone such as for hamstring anterior cruciate ligament reconstruction as well as posterior cruciate or collateral ligament reconstruction.

BACKGROUND OF THE INVENTION

There are currently, numerous techniques and fixation methods for hamstring anterior cruciate ligament (ACL) reconstructions. The majority of techniques for hamstring fixation involve either an interference type device (such as an interference screw) which relies on interference fixation against the graft; or a suspensory type of device (such as EndoButton, Retrobutton, or transfix) which relies on fixation at a distal point away from the graft. Problems that arise from interference fixation include weaker fixation and iatrogenic damage to the graft. This results from the fact that fixation is achieved by interference fit of the screw against the graft within a tunnel/socket. The interference screw cannot be so tight that it amputates the graft but cannot be so loose that there is no interference fixation. Problems that arise from distal fixation include tunnel widening and osteolysis. Distal fixation devices sit on the far cortex and as a result of micro motion cause osteolysis and a phenomenon of "tunnel widening."

A hybrid technique involves the use of a suspension type device (such as woven flat tape) with interference fixation of the woven flat tape with an interference screw on the far cortex. The problem with this particular hybrid technique is that potential risk exists for slippage of the tape against the interference screw and ultimate fixation failure.

SUMMARY OF THE INVENTION

The present inventions relates to a connector for attaching tissue to bone and, more specifically, to a method and device for attaching a connective tissue to bone. For example, the invention may include a connector for attaching a connective tissue such as a tendon or ligament or ligament replacement tissue to bone. The connector may include a sling for supporting and holding the connective tissue. The connector may also include a trap having an anchor end and a sling end that cooperates with the sling. The trap may include a generally tubular section, such as a sleeve, configured to decrease or constrict in diameter upon application of a longitudinal tensile force to the generally tubular section and, more specifically, to the sling end of the connector. The trap may be dimensioned to fit within a tunnel, including a cavity, through bone and may be dimensioned to be press fit into the tunnel through one end of the tunnel. The trap may be configured to cooperate with the sling at the sling end of the trap so that connective tissue held by the sling can emerge from one end of the tunnel. The trap may also be configured so that an interference plug, for example, an interference screw, may be inserted into the tubular section of the trap at the anchor end of the trap positioned at the other or distal end of the tunnel from where the connective tissue emerges to anchor the trap in the tunnel. The trap and sling cooperate so that when the trap and sling are positioned within the tunnel and the trap is anchored in place by the interference plug, a pulling force exerted on the sling will cause the generally tubular section of the trap to constrict more tightly about the interference plug to deter slippage and withdrawal of the trap from the tunnel. The generally tubular section of the trap may also be configured to lengthen, at least somewhat, in the longitudinal direction when a pulling force is exerted on the sling so that the trap constricts more tightly about the interference plug. In one preferred arrangement, the trap may be configured so that the tubular section lengthens a relatively short distance in the longitudinal direction in relation to the length of the trap but sufficient for the trap to more tightly constrict about the interference plug to deter slippage or withdrawal from the interference plug but not so much as to enable the sling to dislodge from or loosen relative to the bone tunnel.

The tubular section of the cylindrical trap may also be dimensioned in diameter to diametrically fit in the tunnel so that a portion of the tubular section of the trap may engage the inner walls of the tunnel, preferably at least at the anchor end of the trap. The trap and sling may also be dimensioned in the longitudinal direction so that the sling and at least a portion of the tubular section of the trap is contained within the tunnel during use. The trap and sling may also be dimensioned so that when positioned in the tunnel during use the connective tissue held at the sling is positioned within the tunnel and a portion of the connective tissue emerges from one end of the tunnel proximate the sling end of the trap and so that the interference plug can be inserted into the tunnel and within a portion of the tubular section at the anchor end of the trap distal to the sling so that the interference plug captures and holds a portion of the tubular section of the trap proximate the anchor end of the trap in frictional engagement with the bone inside the tunnel. For example, the anchor end of the trap may be dimensioned relative to the interference plug so that the interference plug holds at least a portion of the tubular section, or may hold all or substantially all of the tubular portion, of the trap tightly against the bone within the tunnel in interference fit so that when a tensile force is applied at the sling by connective tissue at least a portion of the tubular section of the trap will constrict in inner diameter and tighten about the interference plug to deter slippage from the plug or withdrawal of the trap from the bone. Additionally, the tubular section of the trap may also lengthen somewhat in a longitudinal direction to enable the tubular section to constrict more tightly about the interference plug. In at least one preferred arrangement, the tubular section of the trap should be configured in weave and length relative to the interference plug to reduce or minimize lengthening as much as possible while increasing or creating sufficient diameter constriction to improve grip to deter slippage from the interference plug.

Optionally, the tubular section of the trap may include a braided tubular portion having, for example, a spiral or helical tubular weave so that a tensile force applied at the sling causes the tubular portion of the trap to decrease in inner diameter to more tightly grasp the interference plug. The braided tubular portion may also increase in length in the longitudinal direction when subjected to a tensile force at the sling. For example, the weave may include spiral or helical weaves in clockwise and/or anticlockwise directions. The weave may also include a spiral or helical cylindrical weave. The braided tubular weave may include a warp and weft type weave configured so that a tensile force applied at the sling causes the angle between the warp and the weft to decrease in the longitudinal direction so that the braided tubular portion constricts in inner diameter as the tubular section lengthens.

Optionally, the sling may include a loop for receiving and holding the connective tissue. Alternatively, the sling may include a passageway at the sling end of the trap for receiving and holding the connective tissue. The passageway may pass through the sling end of the trap. Optionally, the sling may also include an eyelet through a wall of the trap at the sling end of the trap for receiving and holding the connective tissue.

The interference plug may also include an interference screw for screwing into the tunnel and into at least a portion of the tubular section, and optionally into all or substantially all of the tubular portion, of the trap at the anchor end of the trap to hold the anchor end of trap in the tunnel.

Optionally, the connector may also include a pull connected with the trap and projecting from the anchor end of the trap to enable the trap to be pulled in the tunnel by the pull. For example, the pull may be in the form of straps or strap ends connected with the trap at the anchor end of the trap.

In a specific arrangement, a connector for attaching connective tissue to bone may include a strap having free ends foldable together to form a loop at one end of the folded strap with a pair of strap lengths extending from the loop and terminating in free ends at the other end of the folded strap. The loop of the strap may provide a sling for holding and supporting the connective tissue. The connector may also include a trap having a generally tubular section, for example, a sleeve, engageable with the strap lengths and configured so that the loop of the strap is suspended from one end of the trap so that a tensile force applied to the loop can constrict the inner diameter of the tubular section of the trap when the trap is anchored in a tunnel through the bone and preferably so that a portion of the tubular section can constrict and more tightly grasp an interference plug or screw used to anchor at least a portion of the tubular section of the trap in the bone tunnel. One of the strap lengths may run generally longitudinally along one side of the tubular section of the trap and the other strap length may run generally longitudinally along the opposite side of the tubular section of the trap. The generally tubular section may include a braided tubular portion that enables such tubular portion to constrict in diameter upon application of a tensile force. The braided tubular portion may include a warp and weft weave configured such that the angle between the warp and the weft decreases in the longitudinal direction upon the application of a tensile force longitudinally of the braided tubular portion so that the braided tubular portion may lengthen, at least somewhat, in the longitudinal direction to constrict or reduce in diameter. The strap may be dimensioned relative to the trap so that the loop end projects from one end of the trap and the free ends of the folded strap project from the other end of the trap. The free ends of the trap may provide a pull to enable the trap to be pulled within the tunnel in the bone.

BRIEF DESCRIPTION OF THE DRAWINGS

The foregoing summary and the following detailed description of the exemplary embodiments of the present invention may be further understood when read in conjunction with the appended drawings, in which.

DETAILED DESCRIPTION OF THE INVENTION

Figure 1:
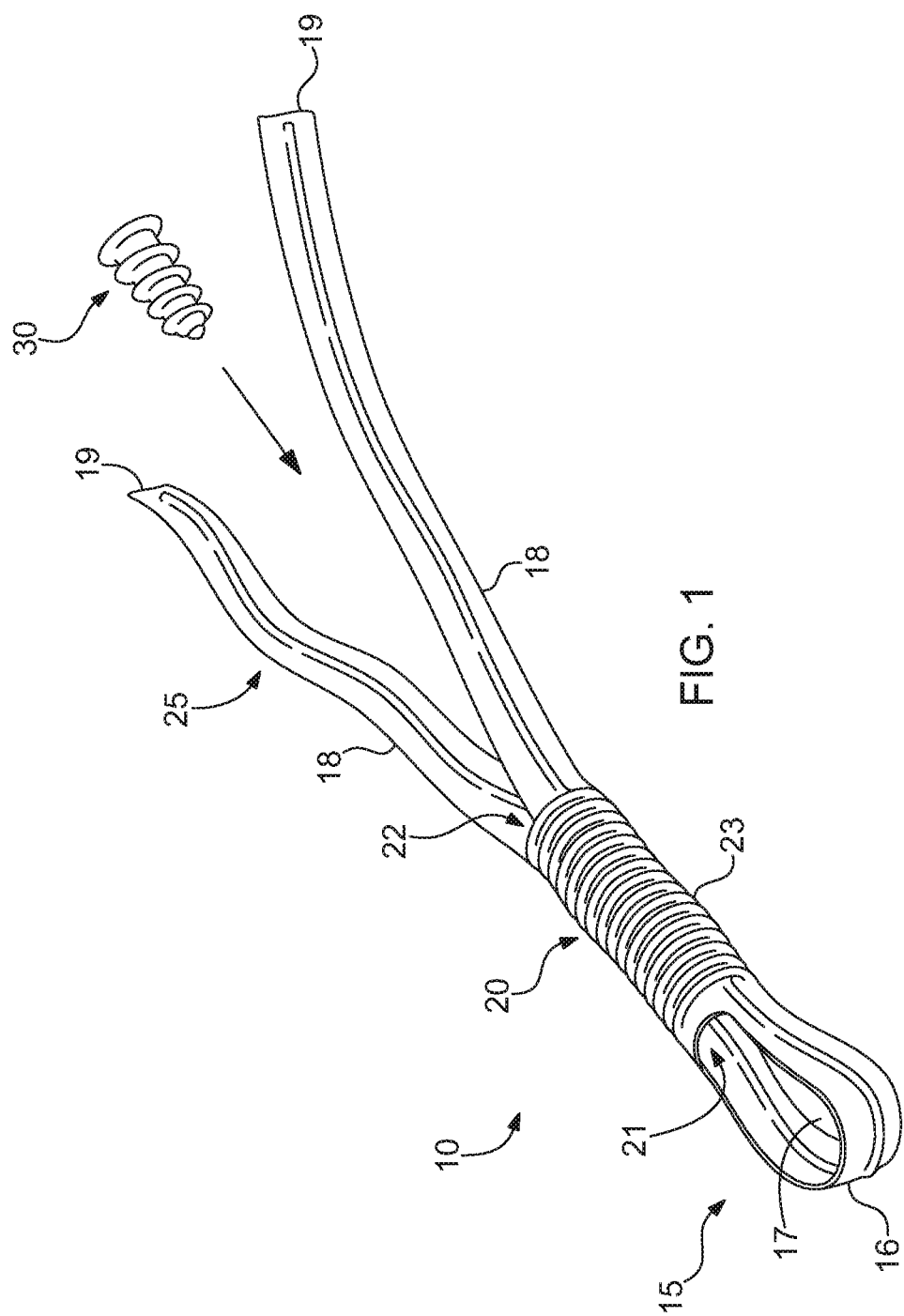
FIG. 1 is a schematic perspective view of a connector for attaching connective tissue to bone using an interference type screw for use with the connector.

Referring now to the figures, wherein like elements are numbered alike throughout, and initially to FIG. 1, a connector, generally designated 10, is depicted for attaching a connective tissue to bone. For example, the connector 10 may be used for attaching a soft tissue graft to bone. In specific application, for example, the connector 10 may be used for soft tissue fixation such as a hamstring anterior cruciate ligament (ACL) reconstruction as well as for other soft tissue fixation such as posterior cruciate ligament (PCL) reconstruction or other collateral ligament reconstructions.

As shown in FIG. 1, the connector 10 includes a sling 15, which may be in the form of a loop 16, for supporting and holding the connective tissue. The connector 10 also includes a trap 20 having a generally tubular section 23, for example, in the form of a sleeve, that is configured to constrict in diameter upon application of a longitudinal tensile force at the loop 16 when the distal end of tubular section is held in position. The trap 20 connects with the loop 16 and is dimensioned to fit, such as press fit, within a tunnel (including a cavity) through bone. The trap 20 is dimensioned so that the connective tissue can emerge from one end of the tunnel and so that an interference plug 30, such as an interference type screw, can be inserted into at least a portion of the tubular section 23, and optionally into all or substantially all of the tubular section 23 that constricts in diameter, at the other end of the trap 20 remote from the sling 15. In this regard, the tubular section 23 of the connector 10 has a sling end 21 where the sling 15 is disposed for capturing and holding the connective tissue and an anchor end 22 remote from the sling end 21 where the plug 30 may be inserted to anchor at least a portion of the generally tubular section 23 to the inner walls of the bone tunnel in tight friction fit or interference fit to hold the connector 10 within the tunnel when a tensile force is applied at the sling.

When used with an ACL hamstring graft, for example, preparation of tibial and femoral sockets or tunnels must be made in which the ACL graft will be pressed fit with the connector 10. In use, a hamstring tendon is typically extracted, stripped, and looped about itself such as by quadruple looping to form a hamstring ACL graft to be suspended h the sling 15 of the connector 10. In this regard, the hamstring tendon is formed into a ring that passes through the eye 17 of the sling so as to interloop and interlink with the sling loop 16 so that such connective tissue is held and captured within the loop 16. The connector 10 is then pressed fit into the tunnel through the bone so that the sling 15 and the portion of the connective tissue held at the loop 16 is contained within the tunnel. A pair of pulls 25 are provided at the anchor end 22 of the trap 20 distal from the sling 15. The pulls 25 may function to enable the connector 10 to be pulled or positioned within the tunnel to properly position the connector within the tunnel. For example, the connector 10 may be dimensioned and positioned in the tunnel so that the connective tissue supported by the sling 15 emerges from one end of the tunnel and so that the pulls 25 connected at or toward the anchor end 22 emerge from the other end of the tunnel. The connector 10 is dimensioned in diameter so that the cylindrical trap 20 diametrically fits within the tunnel and at least a portion of the cylindrical section 23 of the trap engages the inner walls of the tunnel. The connector 10 is also dimensioned longitudinally so that the sling 15 and at least a portion of the tubular section 23 of the trap is contained within the tunnel. Preferably, the tubular section 23 will be contained within the tunnel so that the anchor end 22 of the tubular section 23 is positioned at or near the mouth of the tunnel remote from the sling 15. The tubular trap is dimensioned so that an inference plug, for example, in the form of an interference screw 30, can be inserted within at least a portion of the tubular section provided as a mouth at the anchor end 22 of the trap distal to the sling 15 so that the interference plug captures and holds a portion of the tubular section of the trap at the anchor end of the trap in tight frictional engagement with the bone inside the tunnel. The interference screw 30 functions to screw tightly and anchor the anchor end 22 of the tubular section 23 of the trap 20 tightly against the inner walls of the tunnel within the bone so that when a tensile force is applied at the sling by the connective tissue, at least a portion of the tubular section of the trap will constrict in inner diameter and tighten about the screw to deter slippage or withdrawal of the trap from the screw and the bone tunnel. Optionally, the tubular section of the trap will be configured so that when tightly held within the tunnel by the interference screw, the tubular section of the trap may lengthen in the longitudinal direction when a tensile force is applied at the sling by the connective tissue but preferably only a relatively small distance sufficient to constrict the tubular section more tightly about the screw to further deter slippage or loosening of the connector within the tunnel. For example, the tubular section of the trap may include a braided tubular portion having, for example, helical braids or weaves in opposing spirals, or a spiral or spirals about more longitudinally angled pieces, so that when a tensile force is applied at the sling the braided tubular portion of the trap will decrease in inner diameter to grasp the interference screw more tightly. The braided tubular portion 23 may also increase in the longitudinal direction under the tensile force, but optionally in a relatively small amount in relation to its length but still sufficient to enable the diameter to constrict tighter. The tubular section 23 may also include a braid or a weave having a warp and a weft woven in a configuration so that when a tensile force is applied at the sling the angle between the warp and the weft decreases in the longitudinal direction so that the tubular portion 23 of the trap increases in the longitudinal direction sufficient to decrease in inner diameter to constrict about and more tightly grasp the interference screw to deter slippage from the screw. The generally tubular section 23 may also be in some alternate configuration or weave or braid pattern, for example, having a spiral or helical cylindrical weave, that enables the tubular section 23 to constrict in inner diameter at the anchor end 22 when a tensile force is applied to the loop 16. For example, in one preferred configuration, the trap may be configured to maximize or increase diameter constriction relative to longitudinal lengthening.

The connector 10, as shown in FIG. 1, may be formed from a woven synthetic textile or other suitable material to provide, for example, a woven strap having a generally flat weave. The strap may be looped through the ring of connective tissue and folded over itself to form a loop end 16 at one end of the folded strap with a pair of strap runs or lengths 18 terminating in free ends 19 at the other end of the folded strap. As shown in FIG. 1, the loop end 16 of the folded strap provides a sling 15 having a passageway 17 through which the ring of connective tissue is held and supported. The trap 20 includes a generally tubular section 23, for example, a tubular sleeve, engageable with one of the strap runs or lengths 18 along one portion of or one side of the tubular section and engageable with the other strap run or length along another portion of or along the generally opposite side of the tubular section of the trap so that the loop end 16 is suspended from the sling end 21 at one end of the trap 20 and cooperates with the tubular section 23 of the trap so that a tensile force applied to the loop 16 constricts the inner diameter of the tubular section 23 of the trap when the trap is held in place, for example, when anchored in the bone tunnel. The strap is preferably connected to or with the trap 20. For example, the strap runs or lengths 18 may be attached, for example, by stitching or weaving, to the generally tubular section 23 to secure the loop 16 to the tubular section 23. Also, the tubular section 23 may have a generally uniform diameter, as shown in FIG. 1, or may have a variable or stepped diameter along its length. The strap may also be dimensioned relative to the trap 20 so that the loop end 16 projects from one end, i.e., the sling end 21, of the trap 20 to provide a sling 15 for the connective tissue and so that the free ends 19 of the strap project from the other end, i.e., the anchor end 22, of the trap to provide pulls 25 for the connector. In use, the connector with the ring of connective tissue held in the sling 15 is pressed fit into one end of the bone tunnel and the free ends 19 of the strap are accessed and pulled from the other end of the tunnel until the connector 10 is properly positioned within the tunnel. The connector 10 may be properly positioned so that the loop 16 and the connective tissue held within the loop 16 are contained within the tunnel and the connective tissue emerges from that end of the tunnel. The connector 10 may also be properly positioned within the tunnel so that the generally tubular section 23 or at least a portion of the generally tubular section 23 is contained within the tunnel and the free ends 19 of the strap or at least a portion of the free ends 19 of the strap emerge from the other end of the tunnel remote from the sling 15. The interference screw 30 is then inserted and screwed into the end of the tunnel from which the strap ends 19 emerge. For example, for hamstring ACL reconstruction, the interference screw 30 may be placed into a pre-tapped socket on the far tibial and femoral cortices. The screw 30 is inserted within at least a portion of the generally tubular section 23 of the trap 20 at or near the anchor end 22 of the trap 20 to cause that portion of the tubular section to be captured and held between the screw and the inner walls of the bone tunnel in tight friction fit or interference fit to anchor the connector 10 within the tunnel at the anchor end 22 of the trap 20. Forces that are applied to the connective tissue or graft are tensile forces that are then transferred through the loop 16 to the generally tubular section 23. When a tensile force is applied by the connective tissue to the loop end 16 of the anchored connector 10, the generally tubular section 23 of the connector 10 will tighten and will continue to tighten in inner diameter as the tensile force continues to be applied until the generally tubular section grips about the screw to prevent slippage and/or removal. The generally tubular section 23 may also initially lengthen but optionally only as necessary or only as sufficient or as may be desirable to enable the tubular section to sufficiently tighten about the interference screw 30. At least in one preferred arrangement, the greater the tensile force that is applied, the tighter the grip, at least within limits, of the tubular section 23 onto the screw 30 to resist slippage and pull out.

Figure 2:
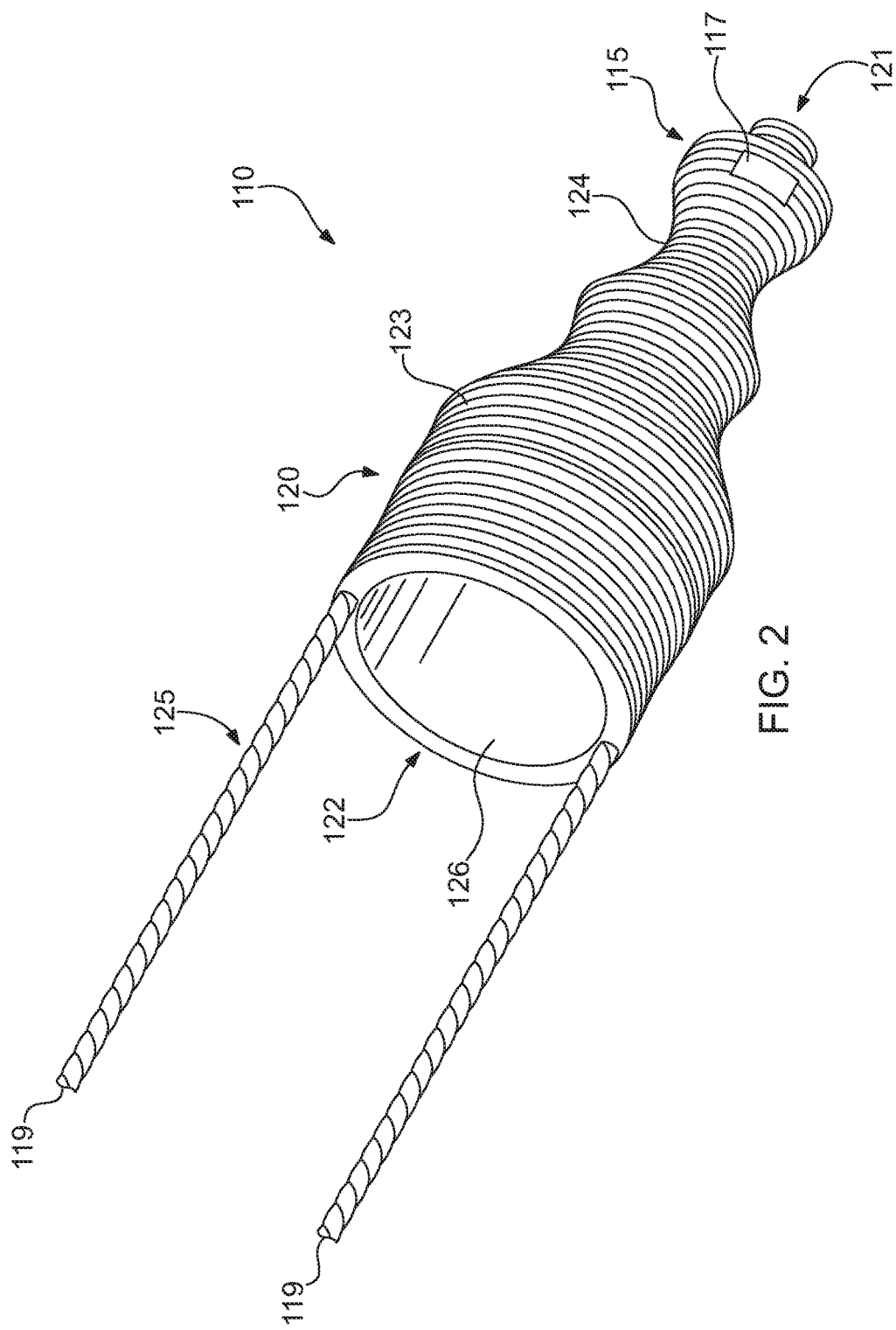
FIG. 2 is a schematic perspective view of a connector for attaching connective tissue to bone having pull straps attached to one end of a generally cylindrical trap and having an eyelet at the other end of the trap for holding the connective tissue.

Referring to FIG. 2, a connector, generally depicted 110, for attaching a connective tissue to bone is depicted. The connector 110 includes a sling 115 for holding and supporting a connective tissue and a trap 120 having a generally tubular section 123 that is configured to contract in inner diameter upon application of a longitudinal tensile force. The connector 110 may have the same weave and braid configurations or arrangements as disclosed in connection with FIG. 1. The connector 110 may be formed from a suitable fabric or material such as a synthetic woven textile. The connector 110 may also be formed, for example, from a material such as polyteraphthalate tape. As shown in FIG. 2, the sling 115 is formed at one end of the connector 110 so that an eye or eyelet 117 passes through a wall at or proximate the sling end 121 of the trap through which the connective tissue may be passed for receiving and holding the connective tissue. As shown in FIG. 2, the connector 110 includes a generally tubular section 123, such as a sleeve, that is not uniform in diameter but is wider at the anchor end 122 of the trap to provide a mouth 126 for receiving the interference screw. The tubular section 123 then narrows down in steps approaching the sling end 121 of the trap to a smaller neck 124, that may be solid and no longer tubular, where an enlarged tip is formed having the eye or eyelet 117 passing therethrough to provide the sling 115. As shown in FIG. 2, the sling 115 and the trap 120 are connected together and may be formed as a single piece or unit rather than as separate parts connected together. A pair of pulls 125 are attached to the trap 120 and may be integrally formed with the generally tubular section 123 at the anchor end 122 of the trap 120 terminating in free ends 119. The connector 110 functions to hold and capture the connective tissue within the eyelet 117 of the sling 115 at the sling end 121 of the trap 120 and connector 110. In use, the connector 110 and the connective tissue are pressed fit within the tunnel through the bone so that the sling end 121 and the portion of the connective tissue held within the sling 115 at eyelet 117 is contained within the tunnel in the bone and so that the connective tissue can emerge from the tunnel from the sling end 121. The generally tubular section 123 of the trap 120 is dimensioned to be contained within the bone tunnel, or so that at least a portion of the tubular section 123 is contained within the tunnel, so that an interference plug such as an interference screw can be inserted into the mouth 126 at the anchor end 122 of the connector 110 to tightly engage the tubular section 123 in tight friction fit or interference fit between the screw and the inner surface of the bone within the tunnel to anchor the connector 110 in position. The pulls 125 can be used to pull the connector through or in the tunnel into proper position from the end of the tunnel remote from the sling end 121. After the connector 110 has been properly positioned, the interference plug or screw can be inserted into the anchor end 122. Preferably, the pulls 127 emerging from the anchor end of the tunnel may be cut flush with the bone at the end of the tunnel. When anchored in place, a tensile force applied to the connector 110 by the connective tissue at the sling 11 will cause the generally tubular section 123 of the trap 120 to constrict in diameter and more tightly grasp the interference screw to deter slippage or withdrawal of the connector 110 away from the interference screw. The tensile force applied by the connective tissue at the sling end 121 may also cause the generally tubular section to increase in longitudinal length but optionally only as necessary or only as sufficient or as may be desirable to enable the tubular section to sufficiently tighten about the interference screw to deter slippage.

Figure 3:
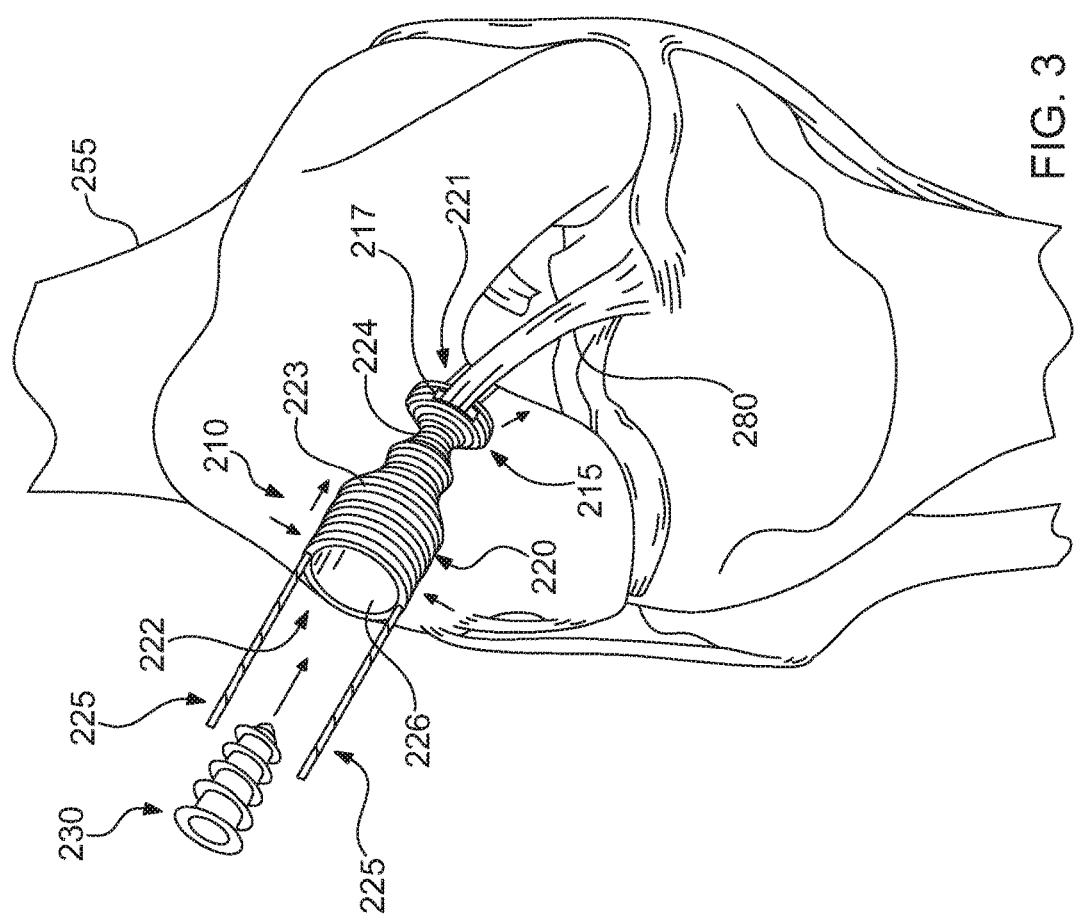
FIG. 3 is a schematic perspective view of a connector for attaching connective tissue to bone shown within a tunnel through the bone having a passageway at a sling end of the trap for providing a sling for supporting the connective tissue in position to emerge from the tunnel through the bone distal to an anchor end of the trap configured for receiving an interference screw and having pull straps affixed thereto.

Referring to FIG. 3, a connector for attaching connective tissue to bone, generally designated 210, is depicted in position within a tunnel through a bone 255. As shown in FIG. 3, the connector 210 includes a sling, generally designated 215, for supporting and holding the connective tissue. As shown, the sling 215 includes an enlarged portion at the sling end 221 of the connector having a passageway 217 therethough to receive and hold the connective tissue. The connector 210 also includes a trap 220 having a generally tubular section 223, such as a sleeve, having a mouth 226 at the anchor end 222 of the connector 210 for receiving an interference screw 230. As shown, the generally tubular section 223 is larger in diameter at the anchor end 222 to provide the mouth 226 for the interference screw 230 and then narrows toward the sling end to form a neck 224 and then again enlarges at the sling end 221 to provide the passageway 217 of the sling 115 for holding and supporting the connective tissue 280. The narrower neck 224 as well as the enlarged section with the passageway 217 may be solid or tubular. As also shown, the generally tubular section 223 need not have a uniform diameter and may in fact change or step in diameter. The connector 210 also includes a pair of pulls 225 connected at the anchor end 222 of the connector 210 to assist in enabling the connector to be pulled or moved into proper position within the bone tunnel. As shown in FIG. 3, the connector 210 is dimensioned in the longitudinal direction so that the sling end 221 and a portion of the connective tissue held within the passageway 217 of the sling 215 is contained within the tunnel and so that connective tissue emerges from the bone tunnel at the sling end 121. The connector 210 is also positioned within the tunnel in the bone so that the tubular section 223 of the trap 220, or at least a portion of the tubular section 223, is contained within the tunnel of the bone to enable an interference screw 230 to be inserted into at least a portion of the tubular section 223, for example, through the mouth 226 at the anchor end 222 of the connector 210 to capture at least a portion of the tubular section between the screw 230 and the inner surface of the tunnel of the bone in friction or interference fit to anchor the connector in place. Again, once the connector 210 is properly positioned, the pulls 227 emerging from the tunnel may be cut flush with the bone. The trap 220 is configured so that when the connector 210 is anchored in proper position by the screw 230 at the anchor end 222 of the tubular section 223, any tensile force applied by the connective tissue on the sling 215 of the connector 210 will cause the diameter of the generally tubular section 223 of the connector to constrict about the screw 230 to more tightly hold the connector is position to prevent slippage or removal. The application of tensile force by the connective tissue at the sling end 221 may also cause the tubular section of the connector 210 to lengthen in the longitudinal direction but again optionally only as necessary or only as sufficient or as may be desirable to enable the tubular section to sufficiently tighten about the interference screw to deter slippage. The connector 210 may be made from suitable materials to perform the necessary functions including the materials previously disclosed. The generally tubular section 223 may be constructed or configured in the configurations or weave or braid arrangements previously disclosed.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

What is claimed is:

1. A connector for attaching a connective tissue to bone comprising a trap having a generally hollow interior portion and having an anchor end positioned at one end of the trap and a tissue holder end positioned at the other end of the trap, the hollow interior portion configured to decrease in diameter upon application of a tensile force at the tissue holder end in a direction tending to pull the tissue holder end away from the anchor end when the anchor end is held in a position to resist the pull, the trap being dimensioned to fit and be contained within a tunnel through the bone so that an interference plug can be inserted into one end of the tunnel for positioning within at least a part of the hollow interior portion of the trap to frictionally engage and hold the anchor end of the trap in position between the interference plug and inner walls of the bone tunnel, and the trap having a tissue holder located in position at the tissue holder end of the trap for holding the connective tissue at the tissue holder end of the trap away from the anchor end so that when a tensile force is applied to the tissue holder in a direction away from the anchor end at least some part of the generally hollow interior portion at the anchor end will constrict more tightly about the interference plug to deter slippage from the plug.

2. The connector of claim 1 wherein the anchor end of the trap is dimensioned in diameter to fit within the tunnel so that at least a portion of the anchor end of the trap may engage inner walls of the tunnel and wherein the trap is dimensioned longitudinally so that the tissue holder at the tissue holder end of the trap and the anchor end of the trap may both be contained within the same tunnel.

3. The connector of claim 1 wherein the trap is dimensioned for positioning within the tunnel in the bone so that the connective tissue held by the tissue holder may be positioned within the tunnel but away from the anchor end and a portion of the connective tissue may extend from the tissue holder and emerge from one end of the tunnel and so that the interference plug can be inserted within at least a portion of the generally hollow interior portion of the trap at the anchor end of the trap distal to the tissue holder to capture and hold at least some section of the trap distal to the tissue holder in frictional engagement with the bone inside the tunnel.

4. The connector in accordance with claim 1 wherein the anchor end of the trap is dimensioned relative to the interference plug so that the interference plug will fit within at least a section of the generally hollow portion of the trap at the anchor end tightly against the bone in interference fit so that when a tensile force is applied at the tissue holder by the connective tissue at least some part of the generally hollow portion of the trap will constrict in inner diameter and tighten about the plug to deter withdrawal of the trap from the bone tunnel.

5. The connector of claim 1 wherein the generally hollow portion of the trap includes a braided tubular section so that tensile force applied at the tissue holder causes the braided tubular section of the trap to decrease in inner diameter to grasp the interference plug more tightly.

6. The connector of claim 5 wherein the braided tubular section includes a warp and a weft weave configured so that a tensile force applied at the tissue holder causes the angle between the warp and the weft to decrease in the longitudinal direction so that the braided tubular section will decrease in inner diameter.

7. The connector of claim 1 wherein the tissue holder includes a loop attached at the tissue holder end of the trap for receiving and holding the connective tissue.

8. The connector of claim 1 where the tissue holder includes a passageway at the tissue holder end of the trap for receiving and holding the connective tissue.

9. The connector of claim 1 wherein the tissue holder includes an eyelet through a wall of the trap at the tissue holder end of the trap for receiving and holding the connective tissue.

10. The connector of claim 1 wherein the interference plug includes an interference screw for screwing into the tunnel and wherein the general hollow portion at the anchor end is configured so that the interference screw may screw into at least a portion of the generally hollow portion of the trap at the anchor end of the trap to hold the anchor end of the trap in the tunnel.

11. The connector of claim 1 including a pull connected with the trap projecting from the anchor end of the trap to enable the trap to be pulled in the tunnel by the pull.

* * * * *